United States Patent [19]

King

[11] Patent Number: 5,562,734

[45] Date of Patent: Oct. 8, 1996

[54] METHOD FOR REDUCING GAMMA RADIATION STERILIZATION INDUCED DISCOLORATION

[75] Inventor: Richard S. King, Warsaw, Ind.

[73] Assignee: Zimmer, Inc., Warsaw, Ind.

[21] Appl. No.: 455,375

[22] Filed: May 31, 1995

[51] Int. Cl.⁶ ................................................. A61F 2/28
[52] U.S. Cl. .......................... 623/16; 623/11; 623/901; 128/898; 433/201.1
[58] Field of Search .................... 128/898; 433/201.1, 433/202.1, 203.1; 623/6, 11, 16, 901

[56] References Cited

U.S. PATENT DOCUMENTS

| | | | |
|---|---|---|---|
| 4,172,702 | 10/1979 | Bernier et al. | 8/4 |
| 4,281,420 | 8/1981 | Raab | 3/1.912 |
| 4,283,799 | 8/1981 | Pratt, Jr. et al. | 3/1.913 |
| 4,336,618 | 6/1982 | Raab | 3/1.913 |
| 4,341,691 | 7/1982 | Anuta | 523/116 |
| 4,491,987 | 1/1985 | Park | 3/1.91 |
| 4,547,327 | 10/1985 | Bruins et al. | 623/16 |
| 4,636,212 | 1/1987 | Posin et al. | 623/66 |
| 4,820,755 | 4/1989 | Webster | 524/88 |
| 4,881,536 | 11/1989 | Noble et al. | 606/94 |
| 5,037,445 | 8/1991 | Sander et al. | 623/66 |
| 5,080,680 | 1/1992 | Mikhail et al. | 623/23 |
| 5,116,380 | 5/1992 | Hewka et al. | 623/23 |
| 5,133,771 | 7/1992 | Duncan et al. | 623/23 |
| 5,331,043 | 7/1994 | Koch et al. | 524/714 |
| 5,472,415 | 12/1995 | King et al. | 623/11 |

FOREIGN PATENT DOCUMENTS

WO94/20046  9/1994  WIPO.

OTHER PUBLICATIONS

Howmedica, Inc.–Precision Strata Hip System–JBJS, Dec. 1993.
Zimmer, Inc.–Harris Precoat Plus Hip Prosthesis–1988.
Zimmer, Inc.–Cement Centralizer Use Review–1992.

Primary Examiner—Paul B. Prebilic
Attorney, Agent, or Firm—Margaret L. Geringer

[57] ABSTRACT

A method for chemically extracting the low-molecular weight chemical additives from a polymethylmethacrylate coating formed on an orthopaedic implant. Specifically, the implant is subjected to a solvent extraction process to remove residual N,N,-dimethyl-p-toluidine, hydroquinone, and methyl methacrylate monomer from the polymethylmethacrylate mass. A solvent such as methanol or hot water does not attack the polymethylmethacrylate but effectively diffuses into the polymethylmethacrylate to extract out these unreacted and residual components. The removal of these components substantially inhibits discoloration and random chain scission in polymethylmethacrylate upon subsequent irradiation for sterilization purposes.

17 Claims, 1 Drawing Sheet

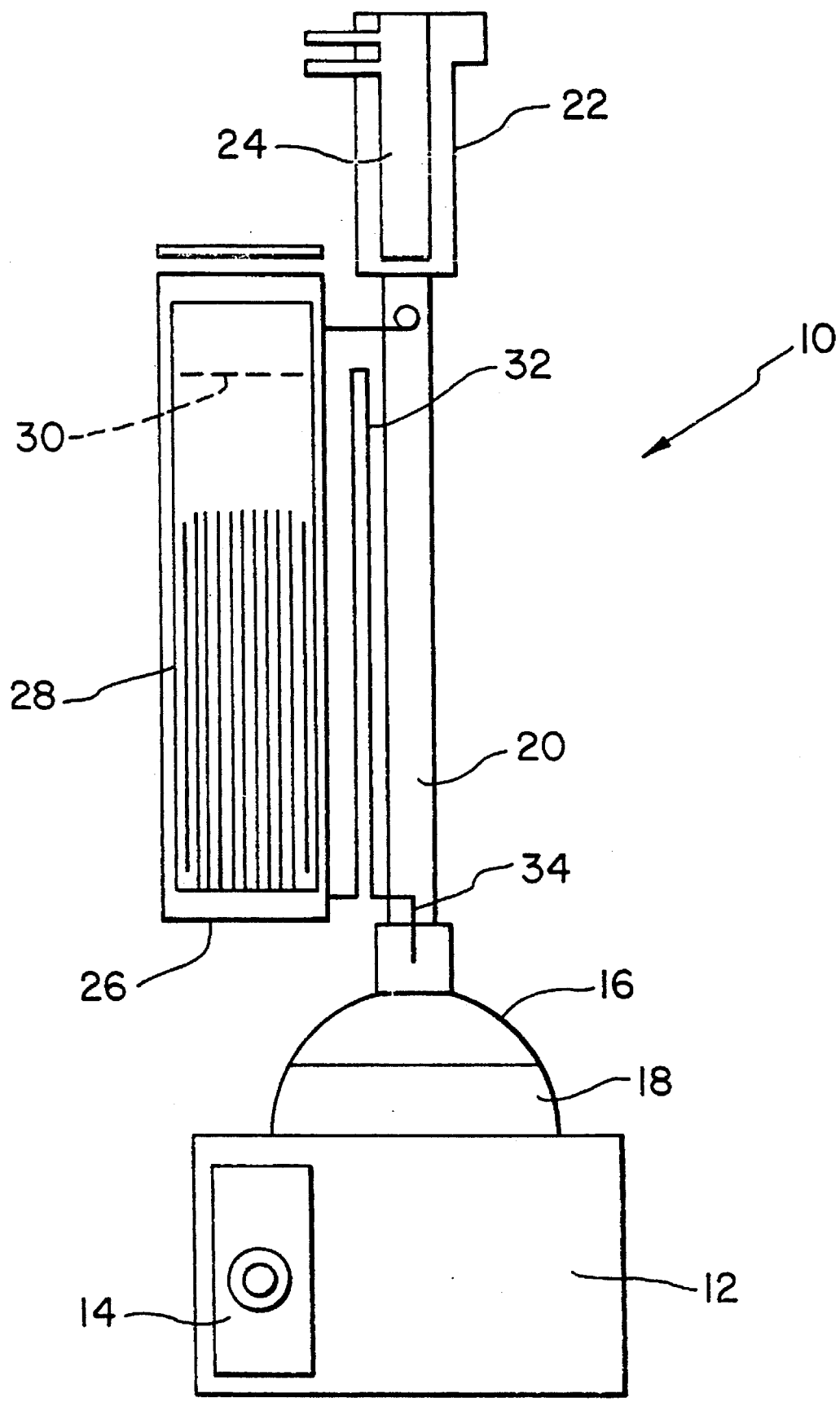

METHOD FOR REDUCING GAMMA RADIATION STERILIZATION INDUCED DISCOLORATION

BACKGROUND OF THE INVENTION

Generally, a prosthesis may be implanted into a bone by forming a cavity into the bone, inserting the prosthesis into the cavity and anchoring the prosthesis to the bone cavity with an adhesive or cement. A common type of bone cement used in retaining a prosthesis in a bone canal comprises a mixture of a liquid monomer component, e.g. methyl methacrylate monomer (MMA), and a polymer powder component, e.g., polymethylmethacrylate (PMMA). The PMMA beads generally contain a small amount of benzoyl peroxide which functions as an initiator when the monomer component and polymer component are mixed. The liquid monomer component includes a small amount of N,N-dimethyl-p-toluidine (DMPT) and hydroquinone (HQ). DMPT promotes cold curing when the liquid monomer component and polymer powder component are mixed. HQ functions as an inhibitor to prevent premature polymerization which may occur under conditions such as heat, light, or chemical reagents. Collectively, the MMA, DMPT, and HQ are referred to as starting materials. The liquid monomer component and powder polymer component are mixed into a paste which is then placed into the bone cavity immediately prior to insertion of the prosthesis stem therein.

In order to maximize the strength of the interface between the prosthesis and the bone cement, the stem of the prosthesis can be precoated in a nonsurgical environment with a polymer coating of PMMA to achieve a chemical bond with the bone cement at the time of surgery. U.S. Pat. No. 4,281,420 discloses the details of how the PMMA coating may be applied to the prosthesis. Such a precoat is typically applied to a metal stem by an electrostatic coating process, with the starting material being a reactor-polymerized PMMA. After insertion of the PMMA precoated prosthesis with the fresh bone cement at the time of implantation, the PMMA coating will become securely bonded to the fresh bone cement as the fresh bone cement polymerizes.

PCT WO 94/20046 discloses a thick polymer or cement mantle which can be preapplied by molding the polymer about the base implant in a nonsurgical or factory environment. This molded polymer layer, like bone cement, is formulated as a self-curing PMMA system. This molded polymer layer relies on a chemical initiator-activator-inhibitor (benzoyl peroxide, DMPT and HQ) system for the self-curing mechanism.

A common method of sterilization is to expose a prosthetic implant to a high energy irradiation process, especially gamma radiation, for a suitable duration. This process can be applied to products through certain types of packaging materials, and as such, is an effective way of providing presterilized packaged products to the customer. However, such radiation can cause the color of the PMMA coating to change from a substantially white or creme or colorless condition to a more yellowed or discolored condition. This is undesirable in that the yellowed or discolored condition is not aesthetically pleasing, and a yellow polymer tends to indicate aging. Accordingly, it is desirable to provide a prosthesis having a polymer coating which remains substantially colorless after radiation sterilization.

SUMMARY OF THE INVENTION

The present invention provides a process in which a polymer coated prosthesis is treated prior to radiation sterilization so that after sterilization, the color of the polymer coating remains substantially unchanged. This is accomplished by solvent extraction of certain components in the cured polymer coating. Specifically, in the case of a PMMA coating, it is desirable to extract the low-molecular-weight chemical additives which are not completely consumed during polymerization. The removal of these residual chemicals effectively reduces radiation-induced discoloration.

In one form of the present invention, a prosthesis coated with a cured PMMA layer or coating is subjected to a solvent extraction process to remove unreacted DMPT, HQ, and residual MMA from the PMMA mass. A solvent such as methanol or hot water does not attack the PMMA but can effectively diffuse into the PMMA and extract out these residual components. It has been found that removal of these unreacted components substantially inhibits discoloration and random chain scission in PMMA upon subsequent irradiation. In addition, residual MMA is removed in the solvent extraction process, thereby reducing toxicity of the PMMA layer.

BRIEF DESCRIPTION OF THE DRAWINGS

The drawing schematically illustrates a solvent extraction arrangement in accordance with the present invention.

DESCRIPTION OF THE PREFERRED EMBODIMENT

The method of the present invention is intended for use with prostheses or orthopaedic implants. Specifically, the method of the present invention is designed for use with implants having a polymer layer or coating fixedly adhered to the outer surface of the prosthetic implant. In one embodiment, the present method relates to implants coated with a PMMA coating, since conventional bone cement is a mixture of PMMA and MMA. However, the method of the present invention is generally applicable to implants having any type of polymer coating or layer thereon. A method of applying a PMMA coating to an implant is disclosed in U.S. Pat. No. 4,281,420, and a method of molding a cement layer to an implant is disclosed in PCT WO 94/20046. Both disclosures are incorporated herein by reference.

In the formation of PMMA, small amounts of low molecular components remain after polymerization is complete. For example, with the molded PMMA layer, these components include DMPT, HQ, and the monomer MMA. There also may be trace amounts of peroxide, such as benzoyl peroxide. The cured PMMA molded layer typically contains 0.2–1.0% (by weight) DMPT, 5–30 ppm HQ, 1.0–4.5% residual MMA, and 0.2–2.0% benzoyl peroxide.

In accordance with the present invention, an implant having a PMMA coating is subjected to a solvent extraction process in order to chemically extract out the residual components in the PMMA coating. Referring to the drawing, there is shown a schematic illustration of a solvent extraction arrangement. The extractor shown is a typical Soxhlet Extractor, although it is noted that any suitable extractor may be utilized in accordance with the present invention, as appropriate. Specifically, there is shown an arrangement 10 having a heating mantle 12 controllable by temperature controller 14. A flask 16 containing a liquid solvent 18 sets on the heater 12. A column 20 vertically extends up from flask 16 to a condenser 22 containing a heat exchanger 24. An extraction tote or chamber 26 is located adjacent column 20 and is in fluid communication therewith. The implant specimens 28 are loosely packed into chamber 26 so that all PMMA coating surfaces are exposed to and in contact with the flow of solvent. One solvent that has performed effectively is methanol. Another suitable solvent is hot water, such as in the 60° to 90° C. range. It is noted that slight modifications to the extraction system may be required when using hot water as the solvent, in order to maintain proper temperatures for the extraction process. However, any solvent that can extract out the residual components without dissolving PMMA is suitable. In addition, a mixed solvent may be used, such as 50% (by volume) ethanol and 50% hot water.

In operation, solvent 18, such as methanol, is heated in flask 16 to its boiling point to covert the liquid to a gas. Since the boiling point of pure liquid solvent is lower than that of any impurities in the liquid, only pure solvent travels up neck or column 20 to condenser 22. Condenser 22 condenses the gas back to a pure liquid, which is then directed or flows into chamber 26. As pure liquid solvent flows into chamber 26, it flows past specimens 28 to saturate the specimens in solvent. The solvent diffuses into the PMMA coating and reacts with the residual MMA, DMPT, and HQ in the PMMA. These residual components are dissolved into the solvent thereby being extracted out of the PMMA.

Solvent 18 accumulates in chamber 26 until the level of solvent reaches a predetermined height 30. Height 30 corresponds to the height of tubing 32, which is in fluid communication with chamber 26. As chamber 26 fills with solvent, a small portion of raffinate flows into tubing 32 so that the height of liquid solvent in tubing 32 always corresponds to the height of liquid solvent in chamber 26. Once tubing 32 is filled, raffinate is siphoned out exit tube 34 back into flask 16. As raffinate flows through tube 34 back into flask 16, pure solvent flows into chamber 26 at the top of the apparatus. The raffinate in the flask is continuously heated to the boiling point of the pure liquid solvent, which is then converted into a gas to maintain the continuous process. The raffinate is replaced with fresh solvent every 1-2 cycles/ hour.

The above arrangement is merely illustrative and other extraction systems may be employed. Such systems include single contact, simple multistage contact, countercurrent multistage contact, continuous countercurrent differential contact, batch countercurrent multistage extraction, countercurrent extraction with reflux, and double-solvent extraction.

In experiments conducted, it has been found that solvent extractions ranging from 2 to 8 hours provide acceptable results. In one experiment, an implant having a molded PMMA layer was subjected to the above solvent extraction process for a duration of two hours. Upon subjecting the treated implant to gamma radiation, some slight discoloration was visibly noticed. Specifically, some yellowing of the PMMA coating was observed. However, the discoloration was substantially less than that which occurs upon subjecting an untreated PMMA coated implant to gamma radiation. Another implant was subjected to the above solvent extraction process for eight hours. Upon subjecting this implant to gamma radiation, almost no discoloration was visible. These experiments verify that the solvent extraction process removes the components from the PMMA that cause discoloration of the PMMA upon subsequent radiation. The slight improvement noted in the eight-hour process over the two hour process clearly suggests that it takes some time for the solvent to diffuse into the center of the PMMA coating.

Although the above experiments were conducted with the solvent methanol, other suitable solvents may be used. In addition, the present invention is applicable to any solvent extraction process used in conjunction with other polymers for use in the medical implant industry which are subjected to subsequent radiation.

It is noted that the polymer layer may suitably have a thickness of up to 1 to 2 mm, although it is not limited thereto. It has also been observed that with methanol as the solvent, swelling of the polymer layer could occur. This may be due to too much of the solvent diffusing into the polymer. Thus, the extraction process should be optimized with regard to the duration of the extraction process in view of the thickness of the polymer layer and the particular implant design and with regard to the particular solvent chosen, as well as with regard to amount of residual components to be extracted out.

It will be appreciated that the foregoing is presented by way of illustration only, and not by way of any limitation, and that various alternatives and modifications may be made to the illustrated embodiment without departing from the spirit and scope of the invention.

What is claimed is:

1. A method for reducing discoloration of a surface of an orthopaedic implant coated with a polymethylmethacrylate layer upon subjecting the implant to gamma radiation, the method comprising the step of subjecting the implant to a solvent capable of chemically extracting out enough of one or more of the following residual materials selected from the group consisting of methyl methacrylate, hydroquinone, N,N-dimethyl-p-toluidine, and peroxide, from the layer so that the polymethylmethacrylate layer substantially retains its original color after the polymethylmethacrylate layer has been exposed to sufficient gamma radiation to sterilize the implant.

2. The method of claim 1, wherein the solvent is methanol.

3. The method of claim 1, wherein the solvent is hot water.

4. The method of claim 1, wherein the implant is subjected to the solvent for a duration ranging from two hours to eight hours.

5. A method for reducing gamma radiation sterilization induced discoloration of an orthopaedic implant, wherein the implant is coated with a polymethylmethacrylate layer containing one or more of the following residual components selected from the group consisting of methyl methacrylate, hydroquinone, N,N-dimethyl-p-toluidine, and peroxide, the method comprising the steps of:

placing the implant in a solvent extraction device;

causing a solvent to pass over the layer for a duration sufficient to chemically extract a sufficient amount of said residual materials to substantially reduce discolorization of said implant upon gamma radiation sterilization; and subjecting the implant to gamma radiation for a duration sufficient to sterilize the implant.

6. The method of claim 5, wherein the solvent is methanol.

7. The method of claim 5, wherein the solvent is hot water.

8. The method of claim 5, wherein the implant is subjected to the solvent for a duration ranging from two hours to eight hours.

9. A method for reducing gamma radiation sterilization induced discoloration of an orthopaedic implant, wherein the implant is coated with a polymer layer containing residual materials that would cause discoloration during gamma radiation sterilization, the method comprising the steps of:

placing the implant in a solvent extraction device; and causing a solvent to pass over the polymer layer for a duration sufficient to chemically extract out a sufficient amount of said residual materials to substantially reduce discolorization of said implant upon gamma radiation sterilization; and subjecting the implant to gamma radiation for a duration sufficient to sterilize the implant.

10. An orthopaedic implant comprising a surface adapted to be fixedly attached to a bone with bone cement, wherein a polymethylmethacrylate layer is adhered to said implant surface, said layer being substantially devoid of residual methyl methacrylate, hydroquinone, N,N-dimethyl-p-toluidine, and peroxide so that said polymethylmethacrylate layer substantially retains its original color after said polymethylmethacrylate layer has been exposed to sufficient gamma radiation to sterilize the implant.

11. An orthopaedic implant comprising a surface adapted to be fixedly attached to a bone with bone cement, wherein an acrylic polymer layer is adhered to said implant surface, said layer being substantially devoid of residual materials that would cause discoloration during gamma radiation sterilization so that said polymer layer substantially retains its original color after said layer has been exposed to sufficient gamma radiation to sterilize the implant.

12. The method of claim 1, wherein the peroxide is benzoyl peroxide.

13. The method of claim 5, wherein the peroxide is benzoyl peroxide.

14. The orthopaedic implant of claim 10, wherein the peroxide is benzoyl peroxide.

15. The orthopaedic implant of claim 11, wherein the residual materials include one or more of the following components selected from the group consisting of methyl methacrylate, hydroquinone, N,N-dimethyl-p-toluidine, and peroxide.

16. A method for reducing gamma radiation sterilization induced discoloration of an orthopaedic implant, wherein the implant is comprised of an outer polymer portion containing residual materials that would cause discoloration during gamma radiation sterilization, the method comprising the steps of:

subjecting the implant to a solvent for a duration sufficient to chemically extract out a sufficient amount of said residual materials to substantially reduce discolorization of said implant upon gamma radiation sterilization; and subjecting the implant to gamma radiation for a duration sufficient to sterilize the implant.

17. The orthopaedic implant of claim 16, wherein the residual materials include one or more of the following components selected from the group consisting of methyl methacrylate, hydroquinone, N,N-dimethyl-p-toluidine, and peroxide.

\* \* \* \* \*

UNITED STATES PATENT AND TRADEMARK OFFICE
CERTIFICATE OF CORRECTION

PATENT NO. : 5,562,734
DATED : October 8, 1996
INVENTOR(S) : King

It is certified that error appears in the above-indentified patent and that said Letters Patent is hereby corrected as shown below:

Columns 5-6:

Please delete Claims 10, 11, 14, and 15.

Signed and Sealed this

Twenty-eighth Day of January, 1997

Attest:

BRUCE LEHMAN

*Attesting Officer Commissioner of Patents and Trademarks*